(12) United States Patent
Nonomura

(10) Patent No.: US 8,093,182 B2
(45) Date of Patent: Jan. 10, 2012

(54) COMPOSITIONS AND METHODS FOR ANTI-TRANSPIRATION IN PLANTS

(76) Inventor: Arthur M. Nonomura, Litchfield Park, AZ (US)

( * ) Notice: Subject to any disclaimer, the term of this patent is extended or adjusted under 35 U.S.C. 154(b) by 1270 days.

(21) Appl. No.: 11/312,169

(22) Filed: Dec. 20, 2005

(65) Prior Publication Data

US 2006/0142158 A1 Jun. 29, 2006

Related U.S. Application Data

(60) Provisional application No. 60/638,868, filed on Dec. 23, 2004.

(51) Int. Cl.
*A01N 25/26* (2006.01)
*A01N 59/04* (2006.01)
(52) U.S. Cl. .......................... 504/100; 504/101
(58) Field of Classification Search .................... 504/119
See application file for complete search history.

(56) References Cited

U.S. PATENT DOCUMENTS

| | | | | |
|---|---|---|---|---|
| 4,338,432 | A * | 7/1982 | Lawson et al. | 536/123 |
| H224 | H | 3/1987 | Malik et al. | 504/206 |
| H303 | H | 7/1987 | Malik et al. | 514/85 |
| 5,413,928 | A * | 5/1995 | Weathers et al. | 435/123 |
| 5,549,718 | A * | 8/1996 | Lerouge et al. | 47/57.6 |
| 5,549,729 | A | 8/1996 | Yamashita | 71/26 |
| 5,634,959 | A * | 6/1997 | Beaty | 71/16 |
| 5,688,981 | A | 11/1997 | Nonomura | 556/116 |
| 5,767,378 | A | 6/1998 | Bojsen et al. | 71/26 |
| 5,797,976 | A | 8/1998 | Yamashita | 71/26 |
| 5,958,104 | A | 9/1999 | Nonomura et al. | 71/11 |
| 5,962,717 | A * | 10/1999 | Nonomura et al. | 556/50 |
| 5,993,504 | A | 11/1999 | Nonomura et al. | 71/27 |
| 6,092,302 | A | 7/2000 | Berrigan | 34/303 |
| 6,258,749 | B1 | 7/2001 | Nonomura | 504/121 |
| 6,309,440 | B1 | 10/2001 | Yamashita | 71/27 |
| 6,318,023 | B1 | 11/2001 | Yamashita | 504/117 |
| 6,358,293 | B1 | 3/2002 | Nonomura | 71/27 |
| 6,407,040 | B1 | 6/2002 | Nichols | 504/140 |
| 6,440,907 | B1 | 8/2002 | Santora et al. | 510/121 |
| 6,464,995 | B1 | 10/2002 | Sekutowski et al. | 424/405 |
| 6,544,511 | B2 | 4/2003 | Nishimura et al. | 424/93.43 |
| 6,699,977 | B1 * | 3/2004 | Gerrish et al. | 536/2 |
| 6,730,537 | B2 | 5/2004 | Hutchison et al. | 438/99 |
| 6,746,988 | B2 | 6/2004 | Hopkinson et al. | 504/127 |
| 6,826,866 | B2 | 12/2004 | Moore et al. | 47/48.5 |
| 2001/0003596 | A1 | 6/2001 | Finnie et al. | 426/106 |
| 2005/0144670 | A1 | 6/2005 | Fujiyama et al. | 800/288 |

OTHER PUBLICATIONS

Guerrini et al.,The effect of calcium chelators on microsomal pyridine nucleotide-linked dehydrogenases of sugarbeet cells, 1994, Oxford Journals, Journal of Experimental Botany, vol. 45, No. 9, pp. 1227-1233.*
Goubet et al. (Identification and Partial Characterization of the Pectin Methyltransferase "Homogalacturonan-Methyltransferase" from Membranes of Tobacco Cell Suspensions, Plant Physiol. (1998) 116: 337-347.*
Goldenkova et al. (The Expression of the Bacterial Gene for Xylose (Glucose) Isomerase in Transgenic Tobacco Plants Affects Plant Morphology and Phytohormonal Balance, Russian Journal of Plant Physiology, vol. 49, No. 4, 524-529.*
Trends in Plant Science, Sep. 1996, vol. 1, No. 9; pp. 296-301; Ray Fall et al. "Leaf methanol-the simplest natural product from plants".
Photosynthesis Research an International Journal-Abstract; vol. 34 No. 1, Oct. 1992; P-522; A.A. Benson et al.; "The path of carbon in photosyntheses: methanol inhibition of glycolic acid accumulation".
Journal of Experimental botany, vol. 54, No. 382, Jan. 2003; pp. 595-604; Sylviane Comparot et al.; "Function and specificity of 14-3-3 proteins in the regulation of carbohydrate and nitrogen metabolism".
Physiologia Plantarum 105: 207-217, 1999; Natalie M. Barratt et al.; "Metabolism of exogenous auxin by Arabidopsis Thaliana: Identification of conjugate Nα-(indol-3-ylacetyl)-glutamine and initiation of a mutant screen".
Plant Physiology, Feb. 2003, vol. 131, pp. 824-837, Sandra Cortes, et al.; "In Plants, 3-O-Methylglucose is phosphorylated by hexokonase but not perceived as a sugar".
Journal of Experimental Botany, vol. 55, No. 398, pp. 791-801, Apr. 2004; Anna Jakubowska et al.; "The auxin conjugate 1-O-indole-3-acetyl-β-D-glycose is synthesized in immature legume seeds by IAGlc synthase and may be used for modification of some high molecular weight compounds".
PNAS Jan. 9, 2007, vol. 104, No. 2, pp. 513-518; Andrew D. Ferguson et al.; "Signal Transduction Pathway of TonB-dependent transporters".
PNAS, Jan. 9, 2007, vol. 104, No. 2, pp. 491-494; H.Ronald Kaback et al; "Site-directed alkylation and the alternating access model for lacy".
Plant Physiology, May 2000, vol. 123, pp. 287-296; Elizabeth Gout et al.; "Metabolism of methanol in plant cells. Carnon-13 nuclear magnetic resonance studies".
Plant Physiology, Dec. 2000, vol. 124, pp. 1532-1539; Susan I. Gibson; "Plant sugar-response pathways. Part of a complex regulatory web".
The Plant Cell, vol. 12, 2395-2408, Dec. 2000; Jamie Lasswell et al.; "Cloning and Characterization of IAR1, a Gene Required for Auxin Conjugate Sensitivity in *Arabidopsis*".
Botanica Marina vol. 45, 2002, pp. 1-8; I.J. Miller et al.; "Evaluation of the structure of the polysaccharides from chondria macrocarpa and ceramium rubrum as determined by 13C NMR spectroscopy".

(Continued)

Primary Examiner — Sreeni Padmanabhan
Assistant Examiner — Timothy E Betton
(74) Attorney, Agent, or Firm — Nields, Lemack & Frame, LLC

(57) ABSTRACT

Methods and compositions comprising design of enlarged pectins are provided. Elaborated pectins are useful for a multitude of functions including surface coating, penetrant, additive and gell. Methods according to the present invention comprise steps for treatments to one or more live pectic cells in one or more compositions that result in modified pectins. In specific embodiments, methods are provided for applying the nanotechnology to live cells for carriage and incorporation of polar compounds.

3 Claims, 3 Drawing Sheets

OTHER PUBLICATIONS

Plant Physiology, Jun. 2004, vol. 135, pp. 989-999; Sherry LeClere et al.; "IAR4, a gene required for auxin conjugate sensitivity in *Arabidopsis*, encodes a pyruvate dehdrogenase E1α homolog".

Proc. Natl. Acad. Sci, vol. 89, pp. 9794-9798, Oct. 1992; A.M. Nonomura et al.; "The path of carbon in photosynthesis: Improved crop yeields with methanol".

Current Opinion in Plant Biology 1999, 2: p. 410-418; Jen Sheen et al.; "Sugars as signaling molecules".

Annals of Botany 95; 707-735; 2005; Andrew W. Woodward et al.; "Auxin: regulation, action, and interaction".

PNAS, Jan. 30, 2007, vol. 104, No. 5; pp. 1445-1446; Robert M. Stroud; "Transmembrane transporters: An open and closed case".

J.Phycol. 33, 800-810 (1997); Valrie A. Gerard; "The role of nitrogen nutrition in high-temperature tolerance of the kelp, *Laminaria saccharina* (chromophyta)".

1981, Australian Journal of Plant Physiology 9 (5) 475-495; A Bacic et al.; "Chemistry and Organization of Aleurone Cell Wall Components From Wheat and Barley"—Abstract.

Plant Cell, vol. 13, 511-520, Mar. 2001; Sabine Carpin et al.; "Identification of a Ca2+-Pectate Binding Site on an Apoplastic Peroxidase".

Eur Biophys J (1998) 27: 127-136; Laurent Catoire et al.; "An efficient procedure for studying pectin structure which combines limited depolymerization and 13C NMR".

Department of Pharmacy; Taylor & Francis vol. 30, No. 4 /2004; 359-367; Kun Cheng et al.; "Insulin-Loaded Calcium Pectinate Nanoparticles: Effects of Pectin Molecular Weight and Formulation pH"—Abstract.

Biomacro Moleculars; Jan. 2004 5(2), 334-341; Fishman et al.; "Nano Structure of Native Pectin Sugar Acid Gets Visualized by Atomic Force Microscopy"—Abstract.

2005, IEEE Transactions on Nanotechnology 4(5): 539-547; Shen et al.; "Synthesis and Characterization of Ni-P-CNT's nanocomposite Film for MEMS Applications"—Abstract.

J. Agric Food Chem. Sep. 2001; 49(9): 4494-501; Fishman ML et al.; "Solvent effects on the molecular properties of pectins"—Abstract.

Annals of Botany 83: 551-557, 1999; Kazuo Ichimura et al.; "Possible Roles of Methyl Glucoside and Myo-inositol in the Opening of Cut Rose Flowers".

Biosci. Biotech.Biochem 61 (10). 1734-1735. 1997; Kazuo Ichimura et al.; "Identification of Methyl β-Glucopyranoside and Xylose as Soluble Sugar Constituents in Roses".

Hort Science 20(5): 879-881. 1985; Marihelen Kamp; "Control of Erysiphe cichoracearum on Zinnia elegans, with a Polymer-based Antitranspirant".

Science Oct. 7, 2005: 121-125; Jisheng Li et al.; "*Arabidopsis* H+-Ppase AVP1 Regulates Auxin-Mediated Organ Development"—1 Page.

Plant Disease/Mar. 1991; vol. 75 No. 3; 231-234; Judith Zekaria-Oren et al.; "Effect of Film-Forming Compounds on the Development of Leaf Ruse on What Seedlings".

Agric. Sci. Digest, 1981, 1 (4): 205-206; M.S. Soundara et al.; "Effect of Antitranspirants and reflectants on Pod Yield of Rainfed Groundnut".

Journal of Horticultural Science (1985) 60 (1) 89-92; N.K. Srinivasa Rao; "The effects of antitranspirants on leaf water status, stomatal resistance and yield in tomato".

Decreux, A. and Messiaen, J. 2005. Wall-associated Kinase WAK1 Interacts with Cell Wall Pectins in a Calcium-induced Conformation Plant and Cell Physiology 46(2): 268-278.

1998, Food and Feed Crops of the United States; Second Edition Revised; G.M. Markle et al.; Descriptive List Classified According to Potentials for Pesticide Residues.

Index of Garden Plants; Mark Griffiths; The Royal Horticultural Society 1992, 1994.

M.Baradas, B. Blad, N. Rosenberg, "Reflectant Induced Modification of Soybean Canopy Radiation Balance v. Longwave Rediation Balance," Agronomy Journal, vol. 68, pp. 848-852 (Nov.-Dec. 1976).

G. Stanhill, S. Moreshet, M. Fuchs, "Effect of Increasing Foliage and Soil Reflectivity on the Yield and Water use Efficiency of Grain Sorghum", Agronomy Journal, vol. 68, pp. 329-332 (Mar.-Apr. 1976).

S. Moreshet, S.Cohen, Y.Fuchs, "Effect of Increasing Foliage Reflectance on Yield, Growth and Physiological Behavior of a Dryland Cotton Crop," Crop Science, vol. 19, pp. 863-868 (Nov.-Dec. 1979).

O.Ziv and R.A. Frederiksen, "The Effect of Film-forming Antitranspirants on Leaf Rust and Powdery Mildew Incidence on Wheat," Plant Pathology. 36 242-245 (1987).

O.Ziv, "Effects of Bicarbonates and Film-Forming Polymers on Cucurbits Foliar Diseases," Plant Disease (May 1992) vol. 76, No. 5, pp. 513-517.

* cited by examiner

Figure 1. Construction of PectiC+.
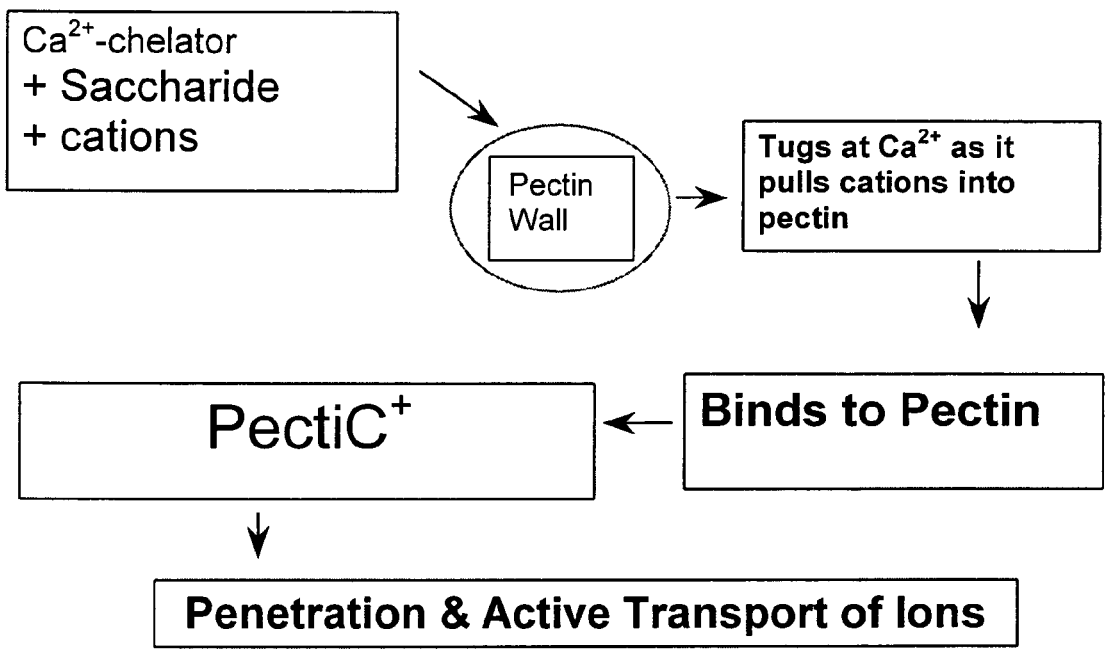

Figure 2. Cob mining process method for pectic components leading to utility.
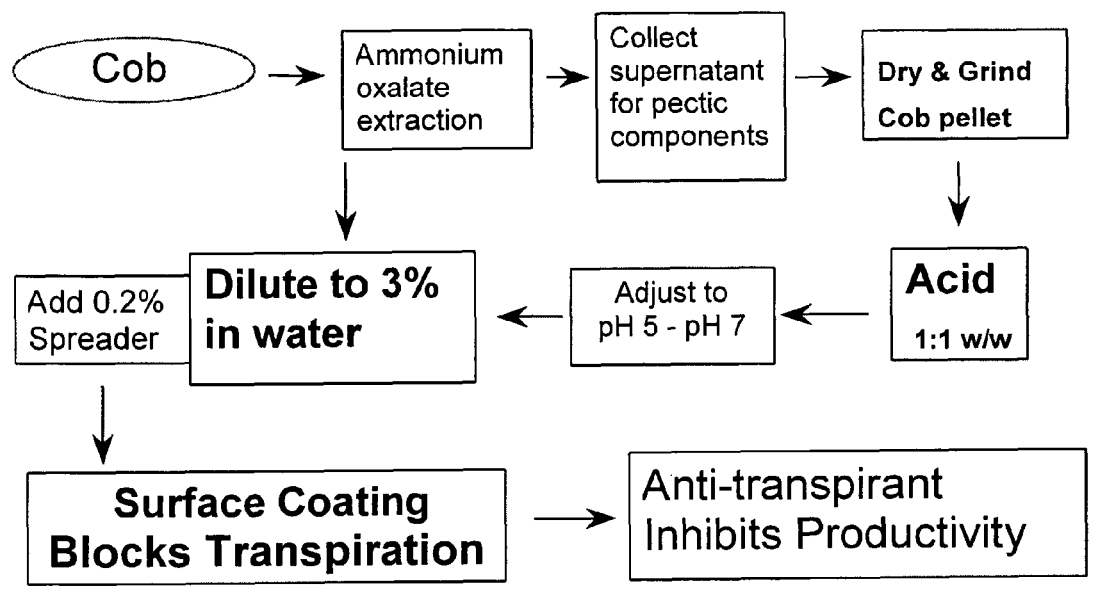

Figure 3. Process for integration of surface coating into PectiC+.

```
Stress Ends  →  Ca²⁺-chelator + surfactant  →  Foliar Spray over Saccharide
                                                           ↓
Cleared Stomata  ←  PectiC⁺ construction
      ↓
Transpiration Resumes
```

US 8,093,182 B2

COMPOSITIONS AND METHODS FOR ANTI-TRANSPIRATION IN PLANTS

This application claims priority of Provisional Application Ser. No. 60/638,868 filed Dec. 23, 2004, the disclosure of which is hereby incorporated by reference.

FIELD OF THE INVENTION

The present invention relates to the nanotechnology of pectins. Methods for construction of pectin-based penetrants of the present invention are presented.

BACKGROUND OF THE INVENTION

Agricultural waste products have developed into massive accumulations throughout the world and are, at best, civic nuisances unless they are converted, somehow, to beneficial utility. Vegetative wastes such as corn cobs are ground into such items as litter absorbents, see for example U.S. Pat. No. 6,092,302, and, even after such manner of use, contribute additionally, again, to the waste stream. At the same time, utilization of biochemical machinery in the field of nanotechnology to achieve practical purposes have tended to focus on fabrication of novel architectures that range from Bucky Balls to metal clusters on DNA scaffolds (see, for example, U.S. Pat. No. 6,730,537; and Shen, G.-R., Cheng, Y.-T., and Tsai, L.-N. 2005. Synthesis and Characterization of Ni—P-CNT's Nanocomposite Film for MEMS Applications. IEEE Transactions on Nanotechnology 4(5):539-547), while purposeful in vivo applications are limited.

The specific focus of the present invention is the ubiquitous cell wall component, pectin. The present invention generally relates to three fundamental designs of pectins: (1) As surface coatings; (2) As novel compositions of matter; and 3) As components that are integrated and transported systemically to the benefit of an entire organism.

In live systems, pectin is involved in the development of all green plants as a key molecule of cell walls. Under the mild conditions of the present invention, cations and saccharides are selected for their similarities to those found in pectin, insuring that they will bind to pectins of the living cell. Natural pectin can be changed, thereby, in size, charge, and function. A new molecule is created as it bonds with cations and saccharides.

Pectins are complexes of heterosaccharides, of which their polygalacutronic acid (PGA) junction zones are characterized by ionic bonds to di-cationic calcium ($Ca^{2+}$). Thus, pectins are $Ca^{2+}$-bearing macromolecules physically measuring in a range of approximately 13 to 45 nm and 41 to 307 kiloDaltons (Fishman M. L., Chau H. K., Kolpak F., Brady J. 2001. Solvent effects on the molecular properties of pectins. J Agric Food Chem. 49(9):4494-501), native pectins averaging 150 to 200 kD (Catoire, L.; Goldberg, R.; Pierron, M.; Morvan, C.; Hervé du Penhoat, C. 1998. An efficient procedure for studying pectin structure which combines limited depolymerization and $^{13}C$ NMR. European Biophysics Journal, 27(2):127-136). Pectin is composed of three main polysaccharides, polygalacturonan, rhamnogalacturonan I and rhamnogalacturonan II. Rhamnogalacturonan I (rhamnosyl and D-galacturonosyl) sections contain hairy branch points with side chains of arabinose and galactose; while rhamnogalacturonan II side chains contain D-xylose, L-fucose, D-glucuronic acid, D-apiose, 3-deoxy-D-manno-2-octulosonic acid, and 3-deoxy-D-lyxo-2-heptulosonic acid attached to polygalacturonic acid (PGA). Gelling properties of pectins depend on esterification, sugars, pH, water, and temperature. Low methoxyl-pectins gel by di-cation bridging forming egg-box junction zones with $Ca^{2+}$. Acyl groups prevent gelation with $Ca^{2+}$; $Na^+$ and $K^+$ non-gelling; and, by nature of carboxylate groups removing $Ca^{2+}$; gelling by divalent cations is ordered $Mg^{2+} \ll Ca^{2+}$ & $Sr^{2+} < Ba^{2+}$. High methoxyl-pectins form two-dimensional molecules with sugar, acid, and water immobilized by H-bonds and hydrophobic interactions. In fact, the ratio of bound sugar to pectin is 100 to 1 w/w (Fishman, M. L., Cooke, P. H., Coffin, D. R. Nano Structure Of Native Pectin Sugar Acid Gels Visualized By Atomic Force Microscopy. Biomacromolecules. 2004. 5(2), 334-341).

The potential for pectin to be modified within the cell wall is evidenced by observations that its bilayered organization remains intact after extraction by water and 8 M urea (Bacic, A. and Stone, B. A. 1981. Chemistry and Organization of Aleurone Cell Wall Components from Wheat and Barley. Australian Journal of Plant Physiology 8(5):475-495). Pectin embedded proteins are integral to catalytic chemical reactions essential to covalent bonds and conformation of electrostatic binding of specific enzymes are ruled by interaction only in the presence of $Ca^{2+}$ (Carpin, S.; Crèvecoeur, M.; de Meyer, M.; Simon, P.; Greppin, H.; and Penel, C. 2001. Identification of a $Ca^{2+}$-Pectate Binding Site on an Apoplastic Peroxidase. Plant Cell, Vol. 13, 511-520); therefore, $Ca^{2+}$ maintains ionic bonds in pectin which change in the living system. Understanding and novel assembly of the above characteristics of pectin were the bases for development of the present invention of in vivo structuring of pectin with $Ca^{2+}$-chelator and saccharide compositions for penetration of exogenous compounds through molecular integration.

Pectin is charged with PGA-chains bearing evenly distributed negative charges; pectin is, thereby, suitable for interactions with positively charged molecules. $Ca^{2+}$-chelators and their cations, especially calcium itself, are the most appropriate candidates for interaction. This feature has proven highly beneficial to methods and compositions of the present invention to transport of any of a variety of nutrients and active ingredients into pectic cells for immediate metabolism.

Specifically, methods and compositions of the present invention include a selection of $Ca^{2+}$-chelators as vehicles for extraction of pectins that motivate interactions of components into cells with a selection of saccharides. In the course of the present invention, chelactant compositions of exogenous sugars and $Ca^{2+}$-chelators develop molecular bonds not only as part of pectin, but also as major exchangeable components of pectin that determine what enters the cell and how weak or strong the bonds will be that allow active transport to occur. According to the concept of the present invention, by designing the normal 100:1 ratio of sugar to pectin to a greater proportion through an import of sugars, the pectin molecule may be enlarged. Add to that, cations in water, and an enhanced number of hydrogen bonds, ionic bonds, and hydrophobicity develop with the integration of exogenous sugars, water and cations into the living cell. For the most part, cations form ionic bonds with pectin. Ionic bonds being some of the weakest of molecular bonds, leave the exogenous cations fully capable of moving internally and throughout an organism by, for example, active transport. Ions are imported and exchanged; urea and ammoniacal nitrogen can be pulled into the cell; and prizing water in pectin gels enhances water-holding capacity of live cells resulting in vigorous enhancement of turgidity for the whole plant. Treatment of live cells with appropriate concentrations of $Ca^{2+}$-chelators in compositions of the present invention causes an ephemeral nanoscalar draw on calcium within pectin, forcing the entire pectin molecule to change. When exogenous chemicals are made available at that time of extraction, ionic, hydrogen and covalent bonds may develop with those compounds. Bonds, however weak or strong, make the exogenous compounds part of the newly formed pectin molecule.

U.S. Pat. No. 5,767,378 provides a method for selecting genetically engineered eukaryotic cells for mannose or xylose metabolism and demonstrated experimentally that xylose is not metabolized as a carbohydrate source. This gives certain indication that, a saccharide composition, of itself, is not an effective penetrant primarily because there is no natural route of metabolism. Recent genetic sequencing reports disclose proteins that code for synthesis of plant recognition or signaling components. However, insertion of genes for synthesis of human sugars in plants (Fujiyama et al. 2005. Plant cell having animal-type sugar chain adding function. United States Patent Application 20050144670 Kind Code A1); and identification of proteins that regulate proton pumps (Li, J.; Yang, H.; Peer, W. A.; Richter, G.; Blakeslee, J.; Bandyopadhyay, A; Titapiwantakun, B; Undurraga, S.; Khodakovskaya, M.; Richards, E. L.; Krizek, B.; Murphy, A. S.; Gilroy, S.; and Gaxiola, R. 2005. *Arabidopsis* $H^+$-PPase AVP1 Regulates Auxin-Mediated Organ Development. *Science* 7 October 2005:121-125), in this class of genetic manipulation bears no relation to in vivo manipulation of pectins of the present invention. Properties of commercial pectin have been characterized based on utilization in food and drug processing and procedures for observing depolymerization (Catoire, L.; Goldberg, R.; Pierron, M.; Morvan, C.; Hervé du Penhoat, C. 1998. An efficient procedure for studying pectin structure which combines limited depolymerization and $^{13}C$ NMR. European Biophysics Journal, Volume 27, Number 2, Pages: 127-136) to loading pectin clusters with pharmaceuticals (Kun Cheng and Lee-Yong Lim. 2004. Insulin-Loaded Calcium Pectinate Nanoparticles: Effects of Pectin Molecular Weight and Formulation pH. Drug Development and Industrial Pharmacy, Volume 30, Number 4:359-367) have been developed; and, as well, manipulation of the gel in food processing, see for example, United States Patent Application 20010003596 Kind Code A1 (Finnie, K. J.; Olsen, R. J.; Frinak, S. C. Jun. 14, 2001. Multi-stage thickening composition for use with packaged food items and process for using same), further evidencing a need for modified pectins; however, prior in vivo manipulation of pectin by application of sugars is not evident. The compositions of the present invention offer systems under which pectins may now be designed and created in a manner that will be of benefit to food and pharmaceutical industries.

Sugars have not been utilized directly as surfactants, but derivative polymers have, as, for example, U.S. Pat. No. 6,440,907 polyoxyethylene derivative of methyl glucoside; and U.S. Pat. No. 6,746,988 alkylpolyglycoside-derivative benoxacor, cloquintocet, dichlormid, fenclorim, fluxofenime, furilazole, and oxabetrinil; and U.S. Pat. No. 6,826,866 alkylpolyglycosidic surfactant-fertilizer.

Methyl glucoside is a natural metabolite in roses that drives buds to senescence (Ichimura, K.; Mukasa, Y.; Fujiwara, T.; Kohata, K.; Goto, R.; and Suto, K. 1999. Possible roles of methyl glucoside and myo-inositol in the opening of cut rose flowers. Annals of Botany 83:551-557). U.S. Pat. Nos. 5,549, 729, 5,797,976, 6,309,440 and 6,318,023 claim utilization of molasses for plant growth promotion. U.S. Pat. No. 5,958,104 utilizes alkyl glucoside as a plant growth regulator; and U.S. Pat. No. 6,358,293 applies methyl glucoside with 20 ppm to 75 ppm manganese, far beyond the range of manganese of the present invention. Polyacylglycosides and polyalkylglycosides of U.S. Pat. No. 6,258,749 enhance plant growth, but do not claim $Ca^{2+}$-chelators. U. S. Statutory Invention Registrations Nos. H224 and H303 described $R(OG)_x$ plant growth regulatory alkylpolyglycosides. U.S. Pat. No. 6,544,511 describes inoculating *Streptomyces* sp. R-5 to a plant for disease resistance wherein xylose is a minor bacterial substrate. Prior art for a $Ca^{2+}$-chelator as saccharide transfer agent and integrator does not exist. For the most part, reference to complexing agents of the prior art is for the acid; whereas, the $Ca^{2+}$-chelators of the present invention are selected from ammonium, diammonium, potassium, dipotassium, tripotassium, sodium and disodium, salts, and the like.

Without limitation to the case at hand, an example considering transfer of major nutrients and micronutrients into plant systems as a consequence of penetration by means of $Ca^{2+}$-chelators is provided. Nutrient deficiency leads to a loss of plant productivity. Plants deficient in a particular element will exhibit symptoms that usually reflect specific elemental limitation. Common symptoms of nutrient deficiency are chlorosis and necrosis. A deficiency of potassium results in growth retardation. Deficiency of zinc causes little leaf. Iron deficiency is indicated by chlorosis in new shoots. Boron deficiency results in bronzing and loss of meristematic growth. Phosphorus deficiency makes leaves turn purple. When such symptoms are exhibited in the field, the crop is curable by supplementation with minerals. In alkaline environments, many minerals may be present, but precipitation makes the metals drop out of solution rendering them unavailable. Incomplete penetration leaves residues at the surface that, upon evaporation of the carrier, may reach toxic concentrations leading to damage. The key is to make the mineral supplement available for metabolism and, although maintaining solubility of metals is most often accomplished through sequestration, conventional agents are not built to penetrate being non-functional within the alkaline boundaries of soaps that are meant to penetrate. U.S. Pat. Nos. 5,688,981, 5,962, 717 and 5,993,504 originate chelactants, ethylenediaminetriacetic acid (ED3A), that are the mildest of their class. A novel class of chemical compound of the present invention, the macrochelactant (Mac), solves the problems of the prior art. When dissolved in water and applied to the phylloplane, this embodiment of the present invention comprises Macs with concentrations of sequestered metals that penetrate efficiently for recovery of a plant from nutrient deficiency. Biologically required metals include potassium, calcium, magnesium, iron, boron, cobalt, copper, manganese, molybdenum, silicon, zinc and nickel; and of these, magnesium and iron are of particular importance, namely, because soluble forms are often depleted. Magnesium precipitates out of alkaline waters and soils. When soluble, magnesium may be incorporated into a chlorophyll molecule. Soluble iron may be utilized for energy transport chains and, in plants, pigmentation improves. One of the major benefits of nutrient supplementation through a Mac is penetration of the entire dose in a manner that leaves no harmful residue on the surface. The complete penetration of, for example, a di-cationic magnesium-Mac results in robust photosynthetic energy transfer and prosperous yields. With particular reference to iron, it is known by convention of prior art that high concentrations, above 1 ppm, are often lethal to foliage, especially when residual iron remains on the surface. Iron and magnesium to facilitate chlorophyll synthesis has, until now, been limited to exceedingly limited exposure, but can be accomplished by Mac processes and compositions of the present invention at many times the conventional dose.

Agricultural formulations contain additives, but prior additives have not been designed from nanotechnological architecture. The utilization of pectins to integrate desired compounds into the cells of an organelle is novel and has broad application throughout the field because molecular incorporation provides an efficient mechanism for transporting desired products into a living system. Exogenous saccharides, of themselves, cannot penetrate foliar cells. Instead, sugars dry into a shiny, sticky surface film on leaves and on exoskeletons of pests. The sugars of the side chains of pectins, i. e., apiose, arabinose, 3-deoxy-D-manno-2-octulosonic acid, 3-deoxy-D-lyxo-2-heptulosonic acid, fucose, galactose, glucuronic acid, and xylose are abundant in cell walls of green plants; and therefore, processes of the present invention mine vegetative waste materials for raw materials. When utilized in surface coatings that do not integrate with cells, specific functions may be blocked by the aforementioned sugars of vegetative waste, providing for exemplary embodiments of the present invention as, for example, growth retardant and anti-transpirant.

U.S. Pat. No. 6,407,040 applied chitin with mannitol to reduce transpiration, but because growth was inhibited by the intact anti-transpirant, U.S. Pat. No. 6,464,995 later enclosed kaolin particulates in the same membrane to allow gas exchange. The use of anti-transpirants has been researched, e.g., Rao, N. K. S. 1985. The Effects of Antitranspirants on Leaf Water Status, Stomatal Resistance and Yield in Tomato, J Hort Sci 60:89-92; Rajan, M. S.; Reddy, K. R.; Rao, R. S.; Reddi, G. H. S. 1981. Effect of Anti-transpirants and Reflectants on Pod Yield of Rainfield Groundnut. Agri Sci Dig 1:205-206; Kamp, M. 1985. Control of *Erysiphe cichoracearum* on *Zinnia elegans*, with a Polymer-based Anti-transpirant. Hort. Sci. 20:879-881; Zekaria-Oren, J. and Eyal, Z. 1991. Effect of Film forming Compounds on the Development of Leaf Rust on Wheat Seedlings. Plant Dis. 75:231-234), and the utilization of any prior anti-transpirant is generally regarded as undesirable because, inherent to its function of blocking evapotranspiration, anti-transpirant films reduce exchange of photosynthetic gases through living plants. Decreased yields have long been directly correlated to the reduction of assimilation inhibiting growth. Clearly, a means of reestablishing normal evapotranspiration would be beneficial to crop management.

A discovery of the present invention solves the problem of lack of penetration of saccharides. On application of $Ca^{2+}$-chelators to saccharides on a pectin surface, the following events of the present invention are observed:

1) $Ca^{2+}$-chelators draw out structural $Ca^{2+}$ and pectin mildly and to a limited extent; 2) Exogenous sugars are pulled in; and 3) Exogenous sugars (and any exogenous cations) bind to pectin. Exogenous saccharides, thereby, not only become part of pectin, they penetrate into the organelle as they do so. As the $Ca^{2+}$-chelator-saccharide is incorporated into the cell, molecular integration is thereby, broadly applicable to any appropriate composition of matter that may be carried along with it into a pectic cell including, without limitation or exclusion of other compounds, active ingredients, inert ingredients, nutrients, and additives. Based on this integrative approach, a novel aspect of the present invention is that after application of a coating that can function as, for example an anti-transpirant, its inhibitory functions are, for the first time, reversible by [applying] molecular integration compositions of the present invention. With foresight, surface coatings may now be designed to penetrate by serial applications of compositions of the present invention.

A reversal mechanism, hereinafter, protranspirant, composition of the present invention that is biodegradable into a cell would be most beneficial and is, therefore, introduced as another embodiment of the present invention. These embodiments of the present invention relate to methods for blocking growth; coatings; anti-transpirant compositions; penetrant saccharides; and protranspirant compositions.

Wilt is symptomatic of a need for a remedy that prevents total crop loss to death, but treatment with an anti-transpirant has been regarded as a drastic measure to take because when transpiration stops, productivity comes to a standstill. Anti-transpirants often coat foliage without penetration to reduce transpirational water loss mechanically. A means of resuming functions to minimize losses would be most beneficial to growers. In a method of the present invention, compositions are applied to shoots of a plant in an effective amount and with a frequency sufficient to retard growth and prevent wilting and then followed by methods that return evapotranspiration to normal function. Compositions and methods of the present invention return the health and yield of crops to their original state by freeing the plant from the drastic effects of conventional anti-transpirants. Exploitation of the growth retardant properties of coatings are also put to benefit by adjusting formulas to retain slowed growth to reduce maintenance without weakening, such as in golf greens; and as a means of preparing a plant towards optimized pesticide response, such as by weakening a weed prior to application of a herbicide. It would be beneficial to buyers to provide these safe compositions from natural products. As pectic components are vegetative, see for example, Decreux and Messiaen 2005 (Wall-associated Kinase WAK1 Interacts with Cell Wall Pectins in a Calcium-induced Conformation Plant and Cell Physiology 46(2):268-278), processes of resourcing waste are also offered.

It would be beneficial to growers to provide safe compositions that integrate nutrients and active ingredients into live cells, making compositions more highly available for plants than previously afforded; that reduce toxicity of essential minerals, additives and active ingredients while making them available; and that penetrate, transfer, transport, spread, emulsify, wet, stick, safen, metabolize, blend and provide other utilizations of active ingredients by entry for greater purpose. The present invention seeks to fulfill these needs and provides further related advantages.

SUMMARY OF THE INVENTION

Problems of the prior art have been overcome by the present invention through provision of methods and compositions for the integration of complex molecules into pectins and for import of compounds. These purposefully designed nanoparticles enable various ingredients to be carried into cells at optimal levels for cellular metabolism. When compositions of the present invention contact cellular pectins, they bind and become part of the living system. Novel compositions of matter, the resultant enlarged pectins, facilitate systemic metabolism. Depending on the introduced component of interest, effects may be enhanced towards the health or destruction of the organism. For example, formulating an appropriate pesticide with compositions of the present invention enhances penetration of, for example, a fungicide and, as a result, the efficacy of destruction of targeted fungi is improved by 30% to 50%, for example. In another embodiment featuring remedial application, what would otherwise be application of inadequate concentrations of ferrous ions to correct chlorotic foliar depletion of micronutrients can instead be turned into a beneficial sufficiency when cations are efficiently transported into cells by the compositions and methods of the present invention. Chlorotic symptoms of iron-deficiency are corrected by highly efficient input of cationic iron and magnesium in $Ca^{2+}$-chelators that turn foliage green.

In yet another embodiment, the water carrier of a $Ca^{2+}$-chelator solution binds the water in a gel formed by hydrogen bonds with pectin, resulting in persistent enhanced turgidity.

By utilization of another embodiment involving separate applications, the coating of the invention may be applied to fulfill a stomatal-blocking antitranspirant function that can be reversed by following with application of a protranspirant.

In a related embodiment of the system, waste vegetation, preferably cobs, are subjected to novel extraction methods that exploit $Ca^{2+}$-chelators to enhance the efficiency of processes that target cob-saccharides to be utilized in the aforementioned solutions.

The methods of the invention may be advantageously utilized with any type of organisms bearing pectins in their cells including, but not limited to, photosynthetic and non-photosynthetic organisms and microorganisms.

BRIEF DESCRIPTION OF THE DRAWINGS

FIG. 1 illustrates diagrammatically, methods leading to the penetration of exogenous components through enlarged pectins of a live cell;

FIG. 2 is a schematic for processing cobs into compositions by drying, grinding, acidifying, and ripening; and application of a non-penetrating surface coating to pectic cells. The diagrammatic illustration shows how the surface coatings of the present invention are applied to plants to block stomata for a reversible anti-transpirant; and FIG. 3 illustrates diagrammatically, methods of the present invention for resuming transpiration through application of Series 2 formulas designed for molecular integration of an anti-transpirant coating that, as a consequence, clears blocked stomata. Optimal assimilation results from this protranspirant.

DETAILED DESCRIPTION OF THE PREFERRED METHODS

The methods and compositions of the invention are designed to treat pectic cells of live tissues and organisms to insure highly efficient transfer of exogenous nutrients, active ingredients, and other ingredients. Of particular interest for transfer into cells are cations, amines, polyamines, fertilizers, pesticides, additives, and adjuvants and all other compounds that may be formulated into compositions of the present invention. Cations are preferred and di-cations are most highly preferred. Treatments of healthy organisms are generally achieved by formulating a $Ca^{2+}$-chelator with a saccharide for systemic active transport.

Most highly preferred divalent cations, such as for example, selections from $Ca^{2+}$, $Fe^{2+}$, $Mg^{2+}$, $Mn^{2+}$ and $Zn^{+2}$, may be sequestered by the aforementioned $Ca^{2+}$-chelators as well as preferred monovalent cations selected from K, $NH_4$; and individually or as blends. Appropriate chelants are essential to penetration of a saccharide whether or not a metal ion is to be introduced because a $Ca^{2+}$-chelator extracts pectin. The most highly preferred $Ca^{2+}$-chelator is the polyamine-polycarboxylate, ethylenediaminetetraacetate, disodium salt ($Na_2EDTA$). Polyamines tend to interact directly with the ionically bound $Ca^{2+}$ in an egg box junction zone of pectin and, when applied in moderation by taking into consideration the number of $Ca^{2+}$ ions available in a cell, a $Ca^{2+}$-chelator can be applied at optimal concentrations designed to give a slight molecular tug to pectin layers that is tolerable to a cell and that maintains it in its living state. The broad concentration of polyamine $Ca^{2+}$-chelators in the compositions of the present invention is about 50 ppm to about 0.5%, and the preferred range is from about 200 ppm to about 1 ppt. After drawing the layered pectin out mildly at physiological levels, exogenous compounds may be introduced within the molecular structure of the affected native pectin. As exogenous saccharides are integrated, they change the charge and physical nature of pectin. Where catalysts abound in a live system, enzymes in pectin have a key role in oligomerization of saccharide to PGA and, thus, play into the enlargement of the molecule. For the purpose of the compositions of the present invention, the oligomerization process is referred to hereafter as glycosyl transfer oligomerization, abbreviated, GTO. This process of binding saccharides to native pectin makes substantial modifications to the molecule that results in the novel pectin molecule composition of matter of the present invention, hereinafter, referred to as the "PectiC+." (The adjective of pectin is, pectic. The capitalized "C" is the elemental scientific notation for carbon, and the plus+ sign symbolizes the addition of organic components and cations to pectin as a result of the systems of the present invention.) Moreover, as a charged molecule, pectic layers relaxed through binding exogenous water, ions, and sugars allows the import of selected ingredients, preferably di-cations, of choice. Preferred saccharides include monosaccharides, disaccharides, and substituted pyranoses. The most highly preferred saccharides are methyl glucopyranosides, xylose, arabinose, and tetramethylglucopyranose. The composition may specify a surfactant, preferably polymeric, in order for the exogenous composition to pass through a waxy cuticular layer. For example, a composition comprising: 1 mM to 100 mM, preferably, 1 mM to 10 mM 1,2,3,4-tetra-O-acetyl-β-D-glucopyranose; plus 0.001 mM to 10 mM $(NH_4)_2EDTA$ is applied in an aqueous solution with a random block copolymer surfactant, preferably at or above its critical micelle concentration (CMC), sprayed directly on shoots of plants. The CMC of commercial EOPO surfactants is within the range of 0.1 to 3 grams/liter, and the preferred range of the present invention for block copolymer surfactants is approximately 1 to 2.5 grams/liter.

In water, hydrogen bonds maintain the integrity of the macromolecular oligomerization of saccharides in pectin. In this manner, solvent water contributes to turgidity, the water holding capacity of an entire plant, in a gel. Specifically, the formulations enable plants to bank water in a gel and metabolize high concentrations of cationic micronutrients between about 0.0001-30 ppm, preferably between about 1-25 ppm, and more preferably between about 5-15 ppm, which would otherwise be unhealthy for a cell, but for the systems of the present invention. Cationic macronutrients such as N, K, Ca, and Mg may be applied within a broad range of 100 ppm to 90% by chelactants.

Unless otherwise defined, all technical and scientific terms employed herein have their conventional meaning in the art. As used herein, the following terms have the meanings ascribed to them.

"Nanometric" refers to a measurement of length that is one billionth of a meter.

"Nanoscalar" refers to a nanometric (nm) size. In reference to the present invention, the nanoscalar composition is approximately 15 to 45 nm across a particle.

"Nanotechnology" refers to the field of study of nanoscalar technologies.

"Molecule" is a particle composed of bonded atoms. For example, a glass of water is a molecule of hydrogen bonds. Pectin is a large and complex molecule with ionic bonds, covalent bonds, and hydrogen bonds holding water, sugars, proteins, glycoproteins and minerals together in a molecule; by which a single macromolecule may be as large as the redwood tree in which it is growing by virtue of continuity of its bonds from cell to cell.

"Exogenates" refer to compositions of matter that originate externally.

"PectiC$^+$" refers to the novel pectic composition of matter of the present invention to which cations and saccharides have been incorporated into the macromolecular heterosaccharide of native pectin. PectiC$^+$ ranges from approximately 25 nm to 50 nm and 200 to 350 kiloDaltons.

"Glycosyl transfer oligomerizatin" (GTO) refers to the binding action of the formative compositions of the present invention comprising a saccharide that penetrates through directed biosynthesis of a PectiC$^+$.

"Surfactant" refers to a surface-active compound that reduces surface tension by wetting or dispersant action. Typical classes include cationic, anionic (e.g. alkylsulfates), nonionic (e.g. polyethylene oxides) and ampholytic surfactants. The most highly preferred surfactants for blends with reducing sugars such as xylose and glucose are non-ionic because they allow better interactions of compositions than cations. Sugar-based, random block copolymer, amine, polyamine, anionic, nonionic, and cationic surfactants are preferred surfactants of the present invention.

"Penetrant" refers to an agent that carries or transfers another compound into the interior of a living cell. Penetrants are distinct from surfactants as, for example, DMSO is a penetrant, but not a surfactant. A composition of the present invention is a penetrant.

"Chelator" refers to a compound that sequesters by molecular clawing action and maintains solubility of minerals. Suitable natural chelators include polysaccharides, carbohydrates, amino acids, amines, polyamines, salicylic acid, peptides, nucleotides, phosphates, tetrapyrrols, water, organic acids with more than one coordination group, lipids, steroids, ferrioxamines, ionophores, phenolics, and triethanolamine, (TEA); while suitable synthetic chelators include 2,2'-bipyridyl dimercaptopropanol, ethylenediaminotetraacetic acid, ethylenedioxy-diethylene-dinitrilo-tetraacetic acid, ethylene glycol-bis-(2-aminoethyl)-N,N,N',N'-tetraacetic acid, nitrilotriacetic acid, and ortho-phenanthroline; and derivatives, thereof. Suitable soluble salts of chelators are selected from ammonium, diammonium, potassium, dipotassium, tripotassium, sodium, and disodium; and cations; and the like. Suitable $Ca^{2+}$-chelators of the present invention are generally selected from water-soluble salts of the chelator because their acids are not generally soluble at practical concentrations, therefore, the polyamine-polyacetics are expressed as their polyamine-polyacetates. For example, EDTA is the conventional abbreviation for ethylenediaminetetraacetic acid; but herein for convenience, it is the abbreviation for ethylenediaminetetraacetate, its soluble form. Other commercially available chelants include acetates, as for example: (ED3A); ethylenediamine-di(-O-hydroxyphenylacetate), (EDDHA); N-(2-hydroxyethyl)ethylenediamine-triacetate, (HeEDTA); diethylenetriaminepentaacetate (DTPA); ethylene glycol-bis-([beta]-aminoethylether)-N,N,N',N'-tetraacetate (EGTA); trans-1,2-diaminocyclohexane-N,N,N',N'-tetraacetate (CDTA); their salts; and derivatives, thereof. The most highly preferred chelators of the present invention are $Ca^{2+}$-chelators that classically extract pectins from the cell wall. The preferred $Ca^{2+}$-chelators may be selected from water-soluble forms of EDTA, EGTA, and CDTA; and ammonium oxalate; their salts; and derivatives, thereof.

"Chelactant" is a portmanteau of chelant combined with surfactant, reflecting the dual-functioning characteristics of the chelactant molecule. When blended in large proportion, exceeding 100:1, saccharide:chelant, compositions of the present invention exhibit chelactant properties and, within the context of the claims of the present invention, chelactant refers to such compositions. In the presence of pectin, bonding of the saccharide composition to PGA results in profound surface activity, and as a consequence, it spreads.

"Macrochelactant" (Mac) refers to a metal-chelactant subset of the present chelactant invention that transports exogenous metal ions into a cell. Suitable Macs include all possible ionic combinations consistent with protistan nutrition. Macs of the present invention are particularly useful in foliar formulations and root dressings. The novelty of Mac permits development of nomenclature; and, as such, Macs of the present invention place the name of the metal(s) first, the chelant(s) second, and followed by the saccharide(s). The $Ca^{2+}$-chelator is a preferred central component. For example, where magnesium (Mg) is a plant mineral nutrient and CDTA is one of a selection of $Ca^{2+}$-chelators and tetramethylglucopyranose (TMG) is a preferred saccharide, the Mac is from Mg-CDTA-TMG. An ephemeral nanoscalar film develops as a result of application of an aqueous suspension in a polar solute, such as in a water molecule with hydrogen bonds. In the large hydrogen-bonded water molecule, application of Mac to a planar pectic cell flows to GTO.

"Plant" refers to any life form which photosynthesizes single carbon fragments to pectins including plants with roots and shoots.

"Retards productivity" refers to decreasing, weakening, or stopping greening, vigor, aesthetic quality, and/or photosynthetic yield of an organism.

"Pectin" refers to a complex heterosaccharide nanoscalar particle composed of three main polysaccharides, polygalacturonan, rhamnogalacturonan I and rhamnogalacturonan II. Rhamnogalacturonan I (rhamnosyl and D-galacturonosyl) sections contain side chains of arabinose and galactose; while rhamnogalacturonan II side chains contain D-xylose, L-fucose, D-glucuronic acid, D-apiose, 3-deoxy-D-manno-2-octulosonic acid, and 3-deoxy-D-lyxo-2-heptulosonic acid attached to polygalacturonic acid (PGA).

"Native pectin" refers to pectin in its natural state prior to modification.

"Pectic cell" refers to organisms or cells of organisms that metabolize pectin or pectin-like heterosaccharides, including those of, plants, animals, fungi, and protistans.

"Percent" or "%" is percent by weight unless otherwise indicated.

"Ppt" refers to parts per thousand by weight.

"Ppm" refers to parts per million by weight.

"Ppb" refers to parts per billion by weight.

"Molar" (M) refers to the moles of elemental or molecular concentration.

"milliMolar" (mM) refers to 0.001×M.

"Active ingredient" refers to ingredients that are intended to have a certain effect on the plant, including listed ingredients cited under regulating pesticides by the Environmental Protection Agency of the United States of America (EPA).

"Pesticide" refers to active ingredients listed under regulating pesticides by FIFRA of the EPA.

"Inert ingredient" refers to other ingredients cited under regulating pesticides by the EPA.

"Nutrient" refers to a beneficial metabolized food. For all living organisms, nutrients are derived from available forms of C, H, O, N, P, K, S, Ca, Mg, Fe, Mn, Zn, Cu, Co, Ni, Mo, B, Cl, and the like. In the present invention, all sources of nutritive elements are considered valid additives, the most highly preferred are cations sequestered by $Ca^{2+}$-chelators.

"Available nitrogen" is nitrogen (N) nutrition that is ready for cellular uptake. Conventional sources of N are selected from ammoniacal, urea, nitrate, amine, fish, waste, and organic nitrogen. The most highly preferred forms of N are defined compounds such as $(NH_4)_2$-EDTA, $(NH_4)_2$-EGTA, ammonium sulfate, ammonium oxalate, ammonium nitrate, urea, calcium nitrate, potassium nitrate, and the like. Acceptable historical lists of N include fertilizers, protein and its derivatives, stabilized nitrogen, steady nitrogen delivery, polymer applications for nitrogen, organic fertilizers, and fertilizer efficiency material; of which, a preferred selection may be Organic Ammonium Sulfate, a commercial blend of ammonia, sulfuric acid, and approximately one-tenth organic compounds.

"Aqueous" with reference to solutions and solvents refers to solutions or solvents that consist primarily of water and can be essentially pure water in certain circumstances.

"Saccharide" refers to monosaccharide, substituted saccharide, disaccharide, oligosaccharide, polysaccharide, and pectin. Pectin and components of pectin are preferred. Sugars of the pectin side chains are preferred monosaccharides of the present invention and include apiose, arabinose, fucose, galactose, glucuronic acid, 3-deoxy-D-manno-2-octulosonic acid, xylose, and 3-deoxy-D-lyxo-2-heptulosonic acid. Saccharides include one or more pyranose, furanose, and/or cyclic or straight chain sugar, including, but not necessarily limited to the following sugars: Aldoses, such as, glyceraldehydes, erythrose, threose, ribose, arabinose, xylose, lyxose, allose, altrose, glucose, mannose, gulose, idose, galactose, talose Ketoses, such as, dihydroxyacetone, erythrulose, ribulose, xylulose, psicose, fructose, sorbose, tagatose; glucopyranose; fructofuranose, fructopyranose, xylopyranose; and their parts and derivatives, e.g., glycuronides, glycosamines, and the like.

"Substituted saccharide" refers to saccharides with a substituted moiety, such as acylglycopyranose, alkylglycopyranose, polyacylglycopyranose, polyalkylglycopyranose, PGR-pyranose, and the like. Tetraalkylglycopyranoses (TMG) and tetraacylglycopyranoses are preferred substituted saccharides of the present invention. Methyl glucopyranosides are the most preferred substituted saccharides of the present invention.

PGR-pyranoses include plant growth regulator-substituted saccharides.

Polyacylglycosides and polyalkylglycosides useful in the formulations and methods of the invention include, but are not necessarily limited to any, $(Alkyl)_n$ glycopyranose, wherein n=2 to 5, its salts and its derivatives, and $(Acetyl)_n$ glycopyranose, wherein n=2 to 5, its salts and its derivatives, including, but not limited to, tetraacetylglycopyranose, tetraacetylglucopyranose, tetraacetylmannopyranose, tetraacetylribofuranose, tetraacetylfucopyranose, tetraacetylxylopyranose, tetramethylglycoside, triacetylglycopyranose, triacetylfucopyranosyl chloride, triacetyladenosine, and methyltriacetyl glucoside; any other polyacyl or polyalkyl conjugated to one or more pyranose, furanose, and/or cyclic or straight chain sugar, including, but not necessarily limited to the following sugars: Aldoses, such as, glyceraldehydes, erythrose, threose, ribose, arabinose, xylose, lyxose, allose, altrose, glucose, mannose, gulose, idose, galactose, and talose; Ketoses, such as, dihydroxyacetone, erythrulose, ribulose, xylulose, psicose, fructose, sorbose, tagatose; glucopyranose; fructofuranose, fructopyranose, xylopyranose; and their parts and derivatives, e.g., glucuronides, glucosamines; and any polyacylpolysaccharide, polyalkylpolysaccharide, and any isomer, metabolite, salt, hydrate, ester, amine, surfactant-linked derivative and other suitable biologically or chemically equivalent derivative, and combination thereof.

Polyacylamine derivatives useful in the formulations and methods of the invention include, but are not necessarily limited to, $(Acetyl)_n$ glycosamine, wherein n=2 to 5, its salts and its derivatives, including, but not limited to, tetraacetylglycosamine, tetraacetylglucosamine, tetraacetyglucosamine, tetraacetylmannosamine, tetraacetylribosamine, tetraacetylfucosamine, tetraacetylxylosamine, tetramethylglycosamine, triacetylglycosamine, triacetylfucosamine chloride, and triacetyladenosine; any other polyacylamine derivative conjugated to one or more pyranose, furanose, and/or cyclic or straight chain sugar, including, but not necessarily limited to the following sugars: Aldoses, such as, glyceraldehydes, erythrose, threose, ribose, arabinose, xylose, lyxose, allose, altrose, glucose, mannose, gulose, idose, galactose, talose; Ketoses, such as, dihydroxyacetone, erythrulose, ribulose, xylulose, psicose, fructose, sorbose, tagatose; glucopyranose; fructofuranose, fructopyranose, xylopyranose; and their parts and derivatives, e.g., glucuronides, glucosamines; and any polyacylglycosamine isomer, metabolite, salt, hydrate, ester, amine, surfactant-linked derivative and other suitable biologically or chemically equivalent derivative and combination thereof.

The following saccharides will neither penetrate nor integrate: pentaacetylglucopyranose, pentaacetylgalactopyranose, pentaacetylmannopyranose, tetradecylmaltoside, and phenyltetraacetylglucoside.

The formulations and methods of the present invention may be applied to virtually any variety of living organism that metabolizes pectins. These organisms include fungi, protistans, animals, and, most preferably, plants. Plants include innumerable agricultural varieties, such as those listed by G. M. Markle, J. J. Baron and B. A. Schneider, Food and Feed Crops of the United States, (Meister Publishing 1998); and by Mark Griffiths, Index of Garden Plants, (Timber Press 1994), the disclosures of which are hereby incorporated by reference. Further, plants which may benefit according to the present invention include, but are not limited to, all plants that have been genetically modified, including hybridized, chimeric, transgenic, cross-bred and mutated plants, and plants comprising recombinant DNA or RNA or plants that have otherwise had their DNA or RNA modified. These lists are intended to be exemplary and are not intended to be exclusive. Other organisms which may benefit by application of the compositions and methods of the present invention will be readily determined by those skilled in the art. Generally, the plant location to which the composition of the method is applied should have a surface area large enough to enable the organism to absorb the composition. Compositions may be applied to all parts of any fungus or protistan. The compositions and methods of the present invention may be applied to virtually any variety of plants, plant parts or associated organism with pectin or pectin-like substance in a cell. Compositions may be applied to all parts of any plant including the shoots, leaves, stems, flowers and/or fruits; and/or roots. For example, it is desirable that the plants include the sprouted cotyledon (i.e., the "seed leaves") or other substantial surfaces that will facilitate absorption, such as the true leaves. Fruit bearing plants may be treated before and/or after the onset of bud, fruit and seed formation.

The compositions of the present invention may also include any of a wide variety of agronomically suitable additives, adjuvants, or other ingredients and components which improve the effects of the compositions of the present invention (hereinafter "additives"). Generally accepted additives for agricultural application are periodically listed by the EPA.

The methods and compositions of the present invention may be used as conventional additives or adjuvants. As adjuvants, the methods and compositions of the present invention would be essential to the efficacy of a product or active ingredient and may be part of a commercial formulation or separately applied. Additives and adjuvants include additions to all agriculturally approved chemicals including chelants, emulsifiers, nutrients, penetrants, safeners, stickers, surfactants, synergists, and wetters.

The penetrant methods of the present invention are achieved by applying appropriate concentrations of a saccharide, or a hydrate thereof or ester derivative thereof or salt thereof with $Ca^{2+}$-chelators to a pectic cell. Suitable non-penetrating coats for use in the methods and compositions of the present invention include saccharide compositions and blends without $Ca^{2+}$-chelator or with a $Ca^{2+}$-chelator, but present at insufficient concentration to penetrate pectin, such as at concentrations below 88 ppm. Appropriate and suitable saccharide components of the invention are selected from monosaccharide, disaccharide, oligosaccharide and substituted saccharide. Specifically, said saccharide component may be preferably selected from pectic side chain sugars, e.g., D-apiose, arabinose, L-fucose, galactose, D-glucuronic acid, and D-xylose; and any raw material or blend or processed sources of saccharides; and pectin, cob-xylose, methyl glucopyranosides, invert sugar, molasses, cane syrup, corn syrup, maltodextrin, malt extract and the like. Of the substituted saccharides, alkyl and acyl substitutions are preferred for least cost. Methyl glucopyranosides, tetraalkylglycopyranoses and tetraacylglycopyranoses are preferred.

The invention provides methods for formulating such additives based on saccharide content. It also provides Mac formulations with ionic metals preferably about 1 ppb to 1000 ppm and applying the same to plants or other pectic cells to safely transport exogenous cations. Mac is designed to enhance input and uptake of massive quantities of metals. Suitable metals of the complex for use in the methods and compositions of the present invention include cationic nutrients such as $Ca^{2+}$, cobalt, copper, iron, magnesium, manganese, nickel, nitrogen, potassium, zinc and the like. Any combinations of Mac components are beneficial and sequestered metals are most highly preferred; for example, zinc-EGTA-xylose. Iron-EDTA-xylose is a preferred composition of the present invention; and, therefore elucidates the composition of 12 ppm iron as 85 ppm EDTA in aqueous xylose suspension. An optional requirement of Mac is for the redox reaction to be balanced, preferably by co-application of nutrients such as urea and ammoniacal nitrogen, in a broad range of 1 lb. to 100 lb. per acre. The most highly preferred form of nitrogen is $(NH_4)_2EDTA$, in the preferred range of 100 ppm to 2000 ppm. The complexing compounds employed in at least the foliar and other compositions of the present invention preferably also comprise a surfactant for application at its CMC. The combination with an ammonium salt is important to balance internal redox reactions. The relative ratio of the metal complex to the ammonia source depends on the route of administration. Appropriate solubilization is achieved, as for example, with iron as soluble ferric and preferably ferrous salts, such as, ferric chloride and ferrous sulfate. Most preferably, mineral complexes of $Ca^{2+}$-chelators are selected from, for example, such $Ca^{2+}$-chelators as ammonium oxalate and EDTA, ED3A, EGTA, CDTA, and the like. Chelant options may include HeEDTA and DTPA, but as trivalents they may be more useful, for trications, for example, ferric-HeEDTA. Water soluble forms of gluconate, lactate, succinate, and like chelants may be included in compositions of the invention to maintain solubility of metals in a surface coating solution. Active ingredients such as a selection of pesticides may be included in a blend for the construction of $PectiC^+$.

It is a primary object of this invention to provide novel compositions of matter that penetrate into a live cell by fusion of the desired product. As a result of the primary invention of $PectiC^+$, methods of utilization are enabled by formulation of safe compositions comprising high concentrations of metals or active ingredients. For example, glyphosate kills plants more efficiently through $PectiC^+$ than as the stand-alone product. In addition, application methods are developed for the formulation of, for example, the enhancement of chlorophyll by iron and magnesium supplementation, without compromising the growth of the plant.

To elucidate the preferred methods of the invention for rendering high concentrations of metals, reference will be made to the example of iron-$(NH_4)_2$EDTA-xylose of the present invention, hereinafter referred to as iron-Mac; without excluding the ability to utilize each and every other nutrient, $Ca^{2+}$-chelator and saccharide combination. As per example, the process with iron representing the general metal component, without exclusion of other metals, comprises the following step: solubilizing one or more salts of a metal in a $Ca^{2+}$-chelator solution. For example, iron may be complexed in solution with $Na_2EGTA$. Metals or ions may alternatively be dissolved in a compatible $Ca^{2+}$-chelator, for example, by dissolving zinc chloride in ammonium oxalate, and etc. For its end use, iron-Mac is further diluted in aqueous solution with iron ions made up to a concentration of between about 1 to 100 ppm and with 25 mM to 100 mM available nitrogen. A suitable volume of the resulting $Ca^{2+}$-chelators with available nitrogen mixture is, thereafter, applied to one or more plants, either to the shoots or the roots, by any suitable application method, such as for example, by foliar spraying, shoot dipping, or root fertigating. The concentration of $Ca^{2+}$-chelators is between about 1 ppm to 1% and preferably between about 6 ppm to 30 ppm metal ion with 88 to 888 ppm $Ca^{2+}$-chelators and 1 mm to 1 M saccharide. Alternatively, solid metals may be utilized at higher concentrations. For example, iron filings may be applied at 1% to 5% iron to turf in a $Ca^{2+}$-chelator-saccharide emulsion, such as 0.3% alkylglycose with 1% iron filings and 100 ppm $(NH_4)_2EDTA$. Nutrient blends may be applied as dry or liquid formations directly to roots and as foliar formulations applied to the shoot of plants. Preferred nutrient sources are ammonium sulfate, ammonium nitrate, ammonium phosphates, urea, potassium nitrate, calcium nitrate, or ammonium chloride. A dry formulation preferably comprises 200 ppm to 500 g $Ca^{2+}$-chelators and 6 grams of ammonium sulfate. Side-dressing delivers a minimum of about 20 mg of dry concentrate per plant. The resulting mixture may be applied dry to the soil and then watered or it may be diluted first in an aqueous carrier and then applied to the roots or shoots such as by foliar spraying or root side-dressing.

To prepare the aqueous mixture, about 1 kilogram of product is diluted in about 100 liters of water or any other suitable aqueous carrier and applied to the plants in an amount consistent with conventional agricultural methods. The preferred volume of application is 100 liters per hectare. The preferred foliar formulation comprises about 1000 g Mac mixed with 3 kilograms urea and diluted in about 100 liters of an aqueous carrier. The method for making and applying a formulation may further comprise the step of adding one or more aqueous surfactants, such as about 0.1% to 0.3% block copolymer surfactant, itself a macromolecule, to the formulation and applying the resulting mixture by spraying to drip on the plant foliage in an amount between about 1 to 5 ml per plant. Although the formulation may be applied to the plant in a solid form, it is often advantageous to provide it in liquid form, such as by dispersing, solubilizing, or otherwise mixing the formulation in an aqueous or agronomically suitable organic solvent or carrier to produce aqueous or organic solutions, dispersions or emulsions containing complexing compounds for application to the plant. In dry form, the component molecules are separate. Appropriate aqueous dissolution activates products. The amount of components which are solubilized in the carrier will depend upon the particular compound selected and the method of application. The formulation may be solubilized in the carrier by adding the compound and allowing the compound to dissolve. In some instances, the application of stirring, agitation, or even heat may facilitate the dissolution in the carrier.

The compositions employed in the methods of the present invention may be applied to plants or animals using conventional application techniques. Plants nearing or at maturity may be treated at any time before and during seed development. Fruit bearing plants may be treated before and/or after the onset of bud or fruit formation. Improved chlorophyll content occurs as a result of the application of appropriate concentrations of select Fe—Mg-Macs of the present invention. The compositions employed in the methods of the invention may also include any of a wide variety of agronomically suitable additives, adjuvants, or other ingredients and components which improve or at least do not hinder the beneficial effects of Mac (hereinafter "additives") to provide the compositions of the present invention. Generally accepted additives for agricultural application are periodically listed by the U. S. Environmental Protection Agency. Spreaders are typically organic alkanes, alkenes, alcohols and polydimethylsiloxanes which provide a sheeting action of the treatment across the phylloplane. Suitable spreaders include paraffin oils, propanol, butanol, and polyalkyleneoxide polydimethylsiloxanes. Suitable surfactants include anionics, cationics, nonionics, and zwitterionics. Surfactants and spreaders may be selected from $C_1$ to $C_8$ alcohols, preferably from methanol, ethanol and isopropanol at concentrations of less than 1% to 90% of the solution.

In addition to the foregoing additives, the compositions of the present invention may also advantageously include one or more conventional nutrients Suitable nutrients for inclusion in the compositions, methods and systems of the present invention will be readily determinable by those skilled in the art and include conventional protistan and plant nutrients containing elements such as nitrogen, phosphorus, potassium, elevated carbon dioxide, peroxides and the like. Phosphate, potassium, and available nitrogen are preferred. In order to support rapid vegetative growth, the most highly preferred formulations may select from $(NH_4)_2$EDTA, nitrate, urea, and ammonium salts, preferably ammonium sulfate, ammonium phosphates or ammonium nitrate, within the supplemental range of 0.2% to 2%. For example, 1% iron-$(NH_4)_2$EGTA-alkylglycoside, may be formulated with the nitrogen source, 0.1% to 12% calcium nitrate. Generally, nutrients may be present in amounts sufficient to maintain growth when a product is applied to the plant. The amount added to the compositions of the present invention will depend upon the plants to be treated and residual nutrients. Formulations including N—P—K supplementation are particularly preferred. The elemental content of nutrients may be selected from aluminum, boron, calcium, carbon, chlorine, cobalt, copper, fluorine, hydrogen, iodine, iron, magnesium, manganese, molybdenum, nickel, nitrogen, oxygen, phosphorus, potassium, silicon, sodium, sulfur, and zinc. Typically, nutrients are included in the amount of between about 10 ppm and about 2500 ppm, preferably between about 800 ppm and about 1800 ppm, and more preferably between about 1% and about 75% by weight of the composition. High potency is achieved by shoot or root application of formulations. Compatible metals are sequestered by $Ca^{2+}$-chelators. Other constituents that may be added to the compositions of the present invention include pesticides, antibiotics, gene therapies, and the like. Compositions of the present invention are particularly well-suited to plant interactions with fungi such that efficacy is heightened, for example, as additives to fungicides such as Tilt®. Among the plant growth regulators (PGR) which may be added to the compositions of the present invention are auxins; brassinolides; cytokinins; gibberellins; amino acids; $N_6$-benzyladenine; kinetin; herbicides; vitamins; and derivatives thereof.

Coapplication with piperonyl butoxide, carbon monoxide, or hydrogen peroxide and other monooxygenase inhibitors tend to inhibit metabolism of products of the invention.

The present invention further provides compositions and methods for utilizing biodegradable coatings as anti-transpirants and protranspirants when applied to plants. The compositions of the present invention are typically applied in series, as aqueous solutions or dry compositions to roots and shoots without limitation from simultaneous or parallel admixture or application.

The method of this invention includes the application of the composition as a first part of a series (Series 1) that coats a leaf surface without penetration. Accordingly, the Series 1 composition is preferably devoid of a penetrating agent (e.g., a $Ca^{2+}$-chelator). The coatings block evapotranspiration, acting as anti-transpirants. When the antitranspirants were applied prior to the imposition of midday-wilt conditions plants remained upright as compared to untreated plants that wilted when subjected to the same stressing environment. The major drawback of antitranspirants is inhibition of growth while gas exchange is blocked.

Application of a Series 2 composition as a second part provides for integration of the coating within the pectin of a cell for resumption of transpiration that establishes optimal photosynthetic gas exchange in plants. Plants treated with Series 1 and Series 2 are productive, healthy and green as compared to untreated plants that wilt for a long duration when subjected to the same environmental conditions.

Series 1 compositions comprise biodegradable coatings that are key ingredients in the composition of the present invention selected from the group consisting of compositions of saccharides without $Ca^{2+}$-chelators.

Series 2 protranspirant compositions comprise $Ca^{2+}$-chelators compositions that transport Series 1 coatings into the cell. Series 2 composition of the present invention may include a selection of Macs that may have the additional function of elemental supplementation. Digestive microbes may be applied, and furthermore, the preferred Series 2 protranspirant composition may aid in the proliferation of protistans that are present in Nature. Rapid microbial digestion of the coating may, therefore, involve both plant and protistan cells. As used herein, the soluble metals of the protranspirant refers to any of the set of protistan nutrients derived from the elements C, H, K, N, O, P, $Ca^{2+}$, Mg, S, Fe, Mn, Zn, Si, Cu, Mo, B, Co, Cl, and Ni solubilized with $Ca^{2+}$-chelators. The minimal protranspirant compositions of Series 2 maybe comprised of $Ca^{2+}$-chelators and available nitrogen; and most preferably $Ca^{2+}$-chelators with protistan nutrients.

Generally, the composition of the invention includes Series 2 compositions in an amount from about 0.1% to about 100% by weight, preferably from about 0.2% to about 25% by weight, and more preferably about 0.2% to 5% by weight based on the total weight of the solution. An effective 0.2% solution can be prepared, for example, by tenfold dilution with water of a 2% aqueous stock solution of cob-aldopentose, $(NH_4)_2$-EDTA, $K_2$-EDTA, Mg—$(NH_4)_2$EDTA, $Ca^{2+}$—$(NH_4)_2$EDTA, Cu—$(NH_4)_2$EDTA, Mn—$(NH_4)_2$EDTA, and Fe—$(NH_4)_2$EDTA and Zn—$(NH_4)_2$EDTA. Protranspirants are present in the composition in an amount from about 0.001% to about 50% by weight, preferably from about 0.1% to about 10% by weight, and more preferably about 0.6% by weight based on the total weight of the composition. Metals are preferably complexed in forms that maintain availability to roots and shoots. For example, iron as soluble ferric and preferably ferrous salts, such as, ferrous chloride, ferrous sulfate, ferrous lactate, ferrous succinate; and most preferably, iron-$Ca^{2+}$-chelators such as soluble salts of EDTA, EGTA, ED3A, CDTA; and ammonium oxalate, and the like. Application of Series 2 protranspirant compositions to plants reestablishes transpiration such that high rates of gas exchange optimize photosynthetic metabolism.

Examples of suitable anti-transpirant additives include stickers, surfactants, emulsifiers, films, membranes, polymers, clays, waxes, paraffins, alcohols, polysaccharides, terpenoids, pinene, and siloxanes. Compositions may impart other desirable effects to plants including, for example, additives to fungicides, herbicides, insecticides, PGRs, nitrogen stabilizers, and like pesticides.

In another aspect, the present invention provides a method for blocking evapotranspiration to intentionally weaken plants. In the method, a Series 1 surface coating composition is applied to a plant that functions to retard growth or weaken an undesirable plant to prepare to kill it with pesticides.

The effectiveness of the method and composition of the present invention in preventing wilting and reinstating transpiration resulting in maximized productivity has proven to be consistently demonstrable in the field. During a period when all plants in the field exhibited midday wilt, the trial plot was given foliar treatments by Series 1 anti-transpirant sprays. Thereafter, the treated plants did not wilt and showed evidence of reduced assimilation. After 3 days, the wilt period ended and Series 2 protranspirant treatments were applied to Series 1-treated plants. Control plants were not given Series 2 treatments and showed lower yields than the plants treated with the complete Series 1 and Series 2 treatments.

Without being limited to the following theory, it is believed that the application of Series 1 anti-transpirants to foliage according to the method of this invention reduces transpiration by coating and, thereby, reducing stomatal apertures through which gases and water vapor are exchanged from within internal spaces of the mesophyll into the atmosphere. In particular, when evenly dispersed with agricultural spreaders and emulsions such as by foliar spray to drip, a Series 1 cob-saccharide component, such as sucrose, dries at the surface to a shiny coating.

When a cob-saccharide is applied to foliage, allowed to dry, and analyzed, the film is found to be the unincorporated saccharide on the leaf surface. Thus, stomatal blockage induced by the cob-coating according to the method of the present invention may be responsible, at least in part, for the reduction in transpiration. By application of high levels of protranspirant $Ca^{2+}$-chelators and protistan nutriment, the cob-saccharide could be integrated with cells, akin to plant biodegradation. As desired, Series 2 protranspirants reverse anti-transpirant effects of the Series 1 compositions that were applied. As much as possible, protistan nutrients sequestered by $Ca^{2+}$-chelators are preferred to provide as high a level of $Ca^{2+}$-chelator as possible, as for example, 100 mM $(NH_4)_2$EDTA, 100 mM $K_2$EDTA, 10 mM $K_3$EDTA, 100 mM $Ca^{2+}$-$Na_2$EDTA, 88 mM Mg—$Na_2$EDTA, and the like. Integration of Series 1 saccharides into PectiC$^+$ opens the portals to transpiration. Series 2 protranspirants have direct impacts on yields because gas exchange permits plant metabolism that contributes to overall productivity. Root treatments, according to the present invention, may also be useful in treating plants prior to transplant to prevent transplant shock and death.

Foliar application of the saccharide compositions of the present invention results in a reduction of stomatal conductivity, which is indicative of stomatal closure. Reduction of stomatal conductivity is translatable to decreased transpiration and lower water use for treated plants.

In general, the methods of the invention comprise the steps of formulating a concentrated Series 1 anti-transpirant in aqueous solution with appropriate additives and applying it directly to shoots and/or roots. Agricultural additives to Series 1 anti-transpirants are selected for even surface distribution to the phylloplane. The concentration of anti-transpirant in the formulations should generally be between about 1 mM to 10 M and more preferably between about 5 mM to 1 M. For specific applications, the anti-transpirant may be dry crystals in highest concentration for root application and 5 mM to 500 mM for foliar application. When diluted in an aqueous carrier, the resulting diluted mixture of anti-transpirant and one or more other anti-transpirants may be applied to foliage in amounts of between 1 gallon to 100 gallons per acre, preferably at about 10 gallons to 20 gallons per acre of plants, wherein the concentration of anti-transpirant is between about 5 mM to 1 M.

In general, the methods of the invention may also comprise the steps of formulating concentrated Series 2 protranspirant compositions to resume transpiration. Series 2 treatments may restart a process that was blocked or otherwise enhance evapotranspiration. Series 2 protranspirants comprise 0.1 ppm to 10% $Ca^{2+}$-chelators. Protistan nutriment may be added in aqueous or organic solution with spreaders and other appropriate additives and active ingredients. Methods for Series 2 protranspirants involve applying the resulting mixture in a dry or liquid form directly to shoots and/or roots, preferably to shoots as a foliar spray. The concentration of Series 2 protranspirant in the formulations should generally be between about 1 nM to 1 M and more preferably between about 20 nM to 888 nM. For specific applications, the Series 2 protranspirants may be dry for root application and 5 nM to 500 mM solutions for foliar application. When diluted in an aqueous carrier, the resulting mixtures of Series 1 anti-transpirants and Series 2 protranspirants are preferably applied to foliage in an amount of about 20 gallons to 100 gallons per acre of plants, wherein the concentrations are between about 5 mM to 1 M. Series 1 and Series 2 compositions may be applied to shoots simultaneously or to shoots and roots simultaneously. For example, a farm tractor may be outfitted both with double saddle tanks for foliar boom sprayers. One of the saddle tanks is filled with the Series 1 anti-transpirant of 0.8% cob-arabinose and 0.02% block copolymer surfactant in aqueous solution. For foliar application, the Series 1 anti-transpirant is pumped through spray nozzles calibrated to 100 gallons/acre foliar spray application. For simultaneous Series 2 protranspirant application, the other tank is filled with a 20 pounds/acre 60% methyl glucosides; 5 pounds/acre to 100 pounds/acre ammonium sulfate; and blend of $(NH_4)_2$-EDTA, $K_2$EDTA, Ca—$(NH_4)_2$EDTA, and Mg—$(NH_4)_2$EDTA; with iron-$(NH_4)_2$EDTA; the broad range of the sequestered protistan nutrients at 8 to 888 ppm concentration. The most commonly available salt of EDTA in commerce, however, is Na$_2$EDTA. The implement is calibrated to the total weight of protranspirant based on the injection of total nitrogen. In this manner, in a single pass, the entire series is applied to the crop. The end of a period of water stress is distinguishable by a rise in turgidity and the grower determines when to terminate further treatments by looking for signs of health in the crop.

Root and/or shoot applications of the complete aqueous PectiC$^+$ compositions of the invention affords improved water use efficiency for treated plants when water molecules are carried in with the solution and bind with molecules of the cell.

Accordingly, in another aspect of the present invention, a method for enhancing the turgidity and reducing water use in plants and crops is provided. In the method, a PectiC$^+$ solution is applied to either shoots or roots during a growing season. For foliar application, the PectiC$^+$ solution application is preferably sufficient to wet leaves by, for example, spraying the solution onto leaf surfaces with appropriate additives. The amount and frequency of the application for turgidity varies, depending upon environmental conditions. PectiC$^+$ treatments improve the water use efficiency of a plant through partitioning to a higher proportion of leaf tissues relative to stem tissues. The application of PectiC$^+$ compositions of the invention to crops has been found to significantly reduce the amount of water used by crops and to increase fruit yield.

Utilization of Waste Vegetation

Treatments may be comprised of saccharide products derived from vegetative waste and utilize Ca$^{2+}$-chelators to efficiently mine waste for target products. Vegetative matter includes any parts of roots and shoots of plants, whereof peanut shells are preferred plant parts; and corn cobs are the most highly preferred plant parts; and all vegetative matter will hereinafter be called cobs for the sake of convenience. Initially, cobs may be processed with Ca$^{2+}$-chelators, the least expensive and most practical being 1% to 90% ammonium oxalate. Extraction of pectic components is achieved in the initial bath of ammonium oxalate after mild heating for several hours, preferably under 0.25 to 1× atmospheric pressure. Conventional pressure cookers are adequate when the exhaust is captured and ammonia is recycled. The aqueous supernatant is collected and pectin is harvested. The remaining cob-pellet is hydrolyzed in acid, selected from mineral or organic acids. The preferred mineral acid includes sulfuric acid, preferred for its supply of essential sulfates. Preferred organic acids are carboxylic acids for supply of metabolized carbon, most preferably acetic acid. Acidification is achieved by immersion of cobs or absorbance by cobs of dilute or concentrated acids. When acid is absorbed by a cob, the acid softens the cob and may release cob particles and components for application. For example, for root or shoot uptake, the acid-treated cobs have added benefits of solubilizing minerals and conditioning the medium. Appropriate acids for carrier cob treatments are inorganic or organic. Preferred inorganic acids include, without exclusion of other sources, 0.5% to 50% sulfuric, nitric, and phosphoric. Preferred organic acids are carboxylates that can be metabolized and include, without exclusion of other sources, 1% to 100% acetic, formic, oxalic, and glycolic. Oxalic acid is highly preferred because on neutralization with ammonium hydroxide, a preferred Ca$^{2+}$-chelator, ammonium oxalate is manufactured. A preferred method of acidification is immersion of dry corn cobs in 5% to 15% sulfuric acid in aqueous solution with mild heating to approximately 50° to 100° C. After the cobs disintegrate, appropriate bases and buffers may be applied to adjust within a range of approximately pH 5 to neutral. The major corn cob components of saccharides, their acetates, and aldopentoses are made available for transpiration events.

In another embodiment, PectiC$^+$ is utilized for transport of desired ingredients into a cell. In the following examples, optimal compositions were determined under horticultural growth conditions in greenhouses and the preferred Ca$^{2+}$-chelator is 3% Ca$^{2+}$-Na$_2$EDTA. The most effective concentration was determined to be about 0.1% cob-xylose, 1 ppt (NH$_4$)$_2$EDTA, 8 ppm iron and 6 ppm Mn as (NH$_4$)$_2$EDTA, in aqueous 0.9% to 88% alcoholic media with 0.2% block copolymer surfactant.

The composition and methods of the present invention generally relate to overcoming prospective crop losses by treating the plants with exogenous Ca$^{2+}$-chelator-saccharide compositions. A wide variety of plants, fungi, protistans, and animals can be advantageously treated by the methods of the present invention. Among the plants that may be treated by the methods are crops in floriculture, horticulture, mariculture, hydroponics, food and fiber crops, landscaping, ornamentals, and gardens.

The following examples are provided to illustrate the methods of the invention and should not be construed as limiting. In these examples, the following compounds were utilized: purified water; iron-Mac; 20 mM to 50 mM ammonium nitrate; and 0.2% surfactant. Abbreviations used in the following examples are defined as follows: "iron-Mac" means iron-(NH$_4$)$_2$EDTA-xylose "zinc-Mac" means zinc-(NH$_4$)$_2$EDTA-methylglucopyranosides; "L" means liter; "ml" means milliliter; "mg" means milligram; "g" means gram; "kg" means kilogram; and "mM" means millimolar. The following are examples of specific formulations according to the present invention that may advantageously be employed in the methods of the invention to treat plants and to enhance the chlorophyll content of foliage. The following examples are intended to provide guidance to those skilled in the art and do not represent an exhaustive list of formulations within the scope of the invention. In general, the methods of the invention comprise the steps of formulating iron-Mac with 20 mM to 100 mM ammoniacal nutrient. The resulting mixture is applied in a dry or liquid form directly to the roots or shoots of the plant. The applied concentration of iron should be between about 5-100 ppm, and preferably between about 10-50 ppm. More preferably, iron-Mac and ammonium sulfate with 0.2% surfactant is applied to shoots in an amount of about 100 liters per hectare, wherein the concentration of iron is about 5 ppm to 20 ppm.

Example 1

Dry Formulation

| Component | Grams |
| --- | --- |
| iron-Mac | 40 g |
| ammonium phosphates | 24 g |

The dry formulation from Example 1 is applied by crop duster to 0.1 hectare containing approximately 2,000 plants. Calculation of the application is based on a minimum of 0.2 g of dry mixture per plant. Alternatively, the dry mixture may be applied to the plant soil directly and then watered in to the roots with irrigation. The concentration of soluble iron of the dry formulation is approximately 1%, which, when applied to the soil directly, is well above the normally distributed concentration of agricultural field treatments.

Example 2

Liquid Formulation

| Component | Amount |
|---|---|
| iron-Mac | 100 grams |
| ammonium phosphate | 3 grams |
| Indican | 10 grams |
| EOPO Surfactant | 50 grams |

Add 20 ppm iron-Mac into water supply. Apply a volume of the liquid formulation sufficient to be evenly distributed to the roots, between about 0.1 ml to 10 ml per plant. The diluted aqueous liquid formulation is about 3× to 10× the normally distributed concentration of conventional agricultural field treatments.

Example 3

Liquid Formulation

| Component | Amount |
|---|---|
| iron-Mac + zinc-Mac | 10 K |
| urea | 100 K |
| Tetramethylglucopyranose | 100 grams |

Apply the mixture, appropriately diluted in water, to 1 hectare of plants. Similarly, the diluted aqueous liquid formulation is substantially higher than the normally distributed concentration of conventional agricultural field treatments.

Example 4

Additive

| Component | Amount |
|---|---|
| Herbicide | As per label |
| 60% Methyl Glucosides | 19 lb. |
| Ammonium sulfate | 2 lb. |
| $Ca^{2+}$—$(NH_4)_2$EDTA | 0.5 lb |
| Nonionic surfactant | 0.6 lb. |

Dilute the mixture in 20 to 100 gallons water. Mix until the compounds are dissolved. Foliar spray the resulting formulation on 1 acre of weeds or over herbicide treated rDNA herbicide-resistant crop (e.g. herbicide resistant soy). Allow 5 h for leaf uptake. The following results showed 20% enhanced efficacy of the herbicide using the formulations of the invention versus conventionally treated controls and with identical quantities of each of the components as separate controls.

Example 5

Foliar Formulation

| Component | Amount |
|---|---|
| Zinc-Mac | 10 g |
| Ammonium phosphates | 3 g |
| Surfactant | 2 g |

Dilute the mixture in an appropriate volume of water. Mix until the compounds are dissolved. Spray the resulting formulation on the plant foliage (e.g. New Guinea Impatiens) so that the foliage glistens. Allow a day for leaf uptake.

The following results are of growth promotion using iron-Mac formulations of the invention versus conventionally cultured controls and with identical quantities of each of the components as separate controls.

| | Additive | | |
|---|---|---|---|
| Plant type | 12 ppm iron-Mac Result | 12 ppm Fe—$Na_2$EDTA Result | 50 mM $(NH_4)_2SO_4$ Result |
| Rice | enhanced chlorophyll | phytotoxic | retarded |
| Lantana | enhanced chlorophyll | phytotoxic | retarded |
| Cabbage | enhanced chlorophyll | phytotoxic | retarded |
| | 20% yield increase for all plant types | 5% reduction for all plant types | 5% reduction for all plant types |

The following are exemplary ranges of effective root application doses based on 10 ml per plant.

| Plant type | Zinc-Mac | $(NH_4)_2SO_4$ |
|---|---|---|
| Geranium | 3 to 12 ppm | 10 to 100 mg |
| Coleus | 2 to 10 ppm | 10 to 50 mg |
| Cabbage | 5 to 20 ppm | 25 to 100 mg |

The following are exemplary ranges of effective foliar application doses based on 100 L/Hectare.

| Plant type | iron-Mac | $NH_4$ |
|---|---|---|
| New Guinea Impatiens | 2 to 6 ppm | 30 to 100 mM |
| Corn | 3 to 12 ppm | 25 to 120 mM |

Example 6

Foliar Anti-Transpirant

| Foliar Anti-transpirant | |
| --- | --- |
| Component | Amount |
| Pentose | 450 grams |
| Spreader | 200 grams |
| Water | 100 liters |

Dilute the entire amount of pentose and spreader in 100 L of water. Mix until dissolved. Apply to 1 acre containing approximately 20,000 plants (e.g. rose). Calculation of application is based on a minimum of 5 mg of dry mixture per plant. Alternatively the dry mixture may be applied without spreader directly to or near roots and then watered in to the roots with irrigation.

Example 7

| Foliar Protranspirant | |
| --- | --- |
| Component | Applied Amount |
| Cob-aldopentose | 400 g |
| Ammonium nitrate | 400 g |
| Potassium phosphate | 50 g |
| IPA-based surfactant | 10 g |
| 12% Ferrous gluconate | 10 ppm Fe |
| 6% Mn—Na$_2$EDTA | 8 ppm Mn |
| 2.5% Mg—(NH$_4$)$_2$EDTA | 88 ppm Mg |

The Series 2 solution contains over 600 ppm total $Ca^{2+}$-chelator. Dissolve Series 2 components in 100 L of water. Apply to the same plants to which Series 1 was applied or to crops that would benefit from improved transpiration. Alternatively, the dry mixture without spreader may be applied directly to the soil near roots and then watered in to the roots with irrigation.

Example 8

Stomatal Conductance and Transpiration in Row Crops. Cotton plants were grown from seed in agricultural fields. Plots were identified approximately at midfield and leaves from alternate branches were treated with Series 1 anti-transpirant and Series 2 protranspirant compositions.

The Series 1 antitranspirant composition was 100 mM methylglucosides with 0.2% Tween® agricultural emulsifier in aqueous solution. The Series 2 protranspirant was formulated from 200 mM methylglucosides, 30 mM ammonium sulfate, 10 mM potassium nitrate, 30 ppm Mg as diammonium-EDTA and 6 ppm Fe as disodium EDTA, 0.2% block copolymer surfactant with isopropanol in aqueous solution. Compositions were both applied to crops as foliar sprays calibrated to deliver 20 gallons per acre. The compositions were applied with manual misters to coat the entire phylloplane on alternate branches of 10 plants in the treatment groups. Control groups were selected from the remaining untreated branches of the same plants to which leaves were sprayed in the same fashion as the treated group, except that the control group received a plant nutrient salt solution without saccharides or $Ca^{2+}$-chelator, but with identical concentrations of nutrients. Both the treated group and the control group were sprayed once at 8:00 AM. At noon, when the remainder of the crop exhibited midday wilt, the leaf surface was viewed with a microscope for open or closed apertures. Stomatal conductance was calculated as a proportion of open to closed stomata counted. Foliar application of Series 1 anti-transpirant resulted in 50% closed stomata over the controls. At the end of the stress period, 3 days after Series 1 application, a Series 2 solution was applied to half of the Series 1-treated plants. The next day, Series 2-treated plants showed 20% of stomata closed as compared to 50% closed in controls. Reduction of productivity showed a direct correlation to stomatal aperture events.

The inherent benefit of the reduction of productivity observed by surface coatings was exploited by utilizing their weakening effects as additives to enhance weed kill of pesticides. In sets of replicated trials, weeds were given tank-mixes with saccharides, herbicides, and ammonium sulfate fertilizer. Perhaps the most widely used herbicide, N-phosphonomethylglycine ($PO(OH)_2CH_2.2NHCH_2COOH$), is commonly referred to as glyphosate, and is most abundantly found formulated as a water-soluble mono-isopropylamine (IPA) salt or sodium salt, hereinafter referred to as glyphosate, meant to include salts, thereof. The preferred formulation of the present invention is a blend of 4 lbs./acre to 5 lbs./acre glyphosate; 10 lbs./acre to 100 lbs./acre of 60% to 100% methyl glucosides in a 1:1 to 3:1 blend with ammonium sulfate; and with optional surfactant. After foliar application, inhibitory methods yielded approximately 50% to 85% improved response of weeds to herbicide and additives over positive controls. With herbicide additive proportion of 1:1, methyl glucosides to organic ammonium sulfates ratio, 100% lethal dose response was achieved with 1 lb/acre glyphosate herbicide. An additional benefit is the reversal of the weakening effect of treatments to plants that have been genetically engineered for herbicide resistance. After treatment with a tank mix of herbicide and Series 1 components, a Series 2 formulation of $Ca^{2+}$-chelators may be sprayed over a Series 1 treatment once the herbicide has killed its targeted weeds. The treatment with the Series 2 formulation is designed to return the herbicide resistant plants to optimal yields and strengthen the crops.

Example 9

Resumed Transpiration in Row Crops

Transpiration of water through a plant acts like an evaporative cooler. Foliage that is cool to the touch indicates a high rate of transpiration. With optimal transpiration rates, leaves cool down; but when transpiration decreases, leaves become hot. Foliar Series 2 protranspirant was applied to half the plots that had been treated with Series 1 anti-transpirant. The Series 1 antitranspirant composition was 50 mM arabinose with 0.1% Pluronic® agricultural surfactant and isopropanol in aqueous solution. The Series 2 protranspirant was formulated from 8 mM arabinose, 50 mM ammonium nitrate, 6 mM monopotassium phosphate, 25 ppm Mg as diammonium-EDTA and 6 ppm Fe as disodium-EDTA, with 0.25% Pluronic® agricultural surfactant. Where required during manufacture, up to 8% isopropanol was added as a defoaming agent. Foliar applications of 3% Series 1 were applied according to skip row protocols on cotton during a two week period of water stress. For every six rows treated with Series 1, the neighboring six rows were skipped with the plants left untreated. One day after the single treatment, the foliage of treated rows was turgid during periods when controls exhibited midday wilt in moist substrates, but leaves measured 3° to 5° warmer than ambient.

Three days after foliar application of Series 1, Series 2 protranspirant was applied by fertigation through roots to half the Series 1 anti-transpirant-treated rows. Foliar temperatures of plants treated with both Series 1 and Series 2 averaged 10° to 15° cooler than wilted controls. Foliar temperatures of plants treated only with Series 1 averaged 3° warmer than ambient.

Heating followed by cooling from changed rates of transpiration corresponds to changes in the rates of gas exchange. Sugarbeet seeds were sown on moist quartz sand. When roots grew to at least 15 cm, matched plants were transplanted into identical plastic culture vessels that receive defined nutrients as 0.25× modified Hoagland's solution. Plants were grown side-by-side out of doors under illuminated conditions in the range of 800 to 1,700 µmol photosynthetically active quanta $m^{-2}s^{-1}$ at leaf level, 7% relative humidity, and 32° day temperature. Experiments were initiated on plants two months after sowing. A kinetic study of the effect of anti-transpirants was conducted on sugarbeet. Baseline gas exchange measurements were taken on all plants and set at unity against which other rates were expressed as a ratio to the baseline. For the Series 1 anti-transpirant foliar treatment, 25 mM cob-aldopentose with 0.1% spreader in water was sprayed to glisten on foliage. After 3 hours, the plants treated with anti-transpirant exhibited a decrease in gas exchange by half as compared against untreated control plants. After confirming anti-transpirant activity, foliar sprays with the protranspirant formulation comprising, 25 mM ammonium sulfate and 6 ppm Mn-($Na_2$)EDTA and 1 mM ($NH_4$)$_2$-EDTA were applied. Three hours later, protranspirant-treated plants exhibited rates of gas exchange that averaged 20% greater than controls. During the next two days, the positive effect of the protranspirant formula maintained the resumed ratio of assimilation to transpiration. These results show that both anti-transpirant and protranspirant act rapidly. The results are summarized in the table, below.

| Treatment | n | Gas Exchange |
|---|---|---|
| Baseline | 10 | 1 |
| Series 1 | 5 | 0.5 |
| Series 2 | 5 | 1.2 |

Example 10

When practical, a return to maximized productivity is the important outcome of resumed transpiration. To maintain competitive finances, various formulations derived from vegetative wastes were tested against controls. Major components of corn cobs are cellulose, cellulose acetate, xylose, arabinose, ribose, glucose, and fructose. As a major cob component, cob-xylose was selected for assay in order to eliminate artifacts. As a control check, cob-xylose was assayed by Benedict's copper reaction and, in Series 1 application, a shiny reflective film deposited on the leaf surface was rinsed and collected and found to be comprised of the cob-xylose that was applied. This led to the conclusion that xylose applied to foliage is not metabolized by the plant. Cob-xylose created a surface coating blocking stomata and performing as an effective anti-transpirant. Controls were set up on separate plots to which identical concentrations of separate nutrients and $Ca^{2+}$-chelator were applied. As a means of checking the influence of concentrations of nutrients, it was concluded that these nutrient controls did not show significant gains in growth over untreated controls. Other conventional controls were from plots that were not treated with solutions of the present invention, but that were cultured according to best practices. Each plot consisted of 36 plants in matched populations. Foliar treatment of each plot was achieved by measured volume sprayers with 6 ml of solution. The quantity of saccharides taken up by foliage was computed based on molar concentration per unit area. The sugar content increased by over 50% corresponding to average dry weight increase. From calculations, then the ratio of sugar to pectin ratio was greater than 150:1. The size of PectiC$^+$ was estimated from dialysis exclusion membrane methods modified from (Catoire, et al 1998). Increases in turgidity were supported by comparisons of live weights of populations.

At the end of the test period, shoots were harvested, weighed live and after drying to compare populations. Statistically significant results of treatments with various formulations, at 95% confidence intervals were accepted. Plants treated with Series 1, alone, showed no statistically significant yield difference over controls. Plants treated with Series 1 and Series 2 showed 10% to 41% greater yields than plots treated solely with Series 1. Formulation of Series 2 with a carboxylate or lower alcohol enhanced the yields over mineral salts alone. Following Series 1 and Series 2 treatment, leaf expansion was enhanced over controls by 70% averaged statistically significant levels when plants were cultured under drought conditions. Although this was a surprising result, it is consistent with expansion of cell walls through PectiC$^+$ acquisition of polar particles of the present invention.

Example 11

Upplause™

100 gallons of Mac was formulated within the following specifications under the product name Upplause™ and applied as a foliar spray for correcting iron and magnesium deficiency to 100 acres of corn. Recommended dose was 1 gallon Upplause™ dissolved per 100 gallons of water as applied at a volume of 100 gallons per acre. As a result, greenness of the corn crop was visibly enhanced and corrections of all nutrient deficiencies were successful. Foliar applications were repeated every two weeks, as needed.

| Upplause ™ | Gallons |
|---|---|
| Water | 1-70 |
| 2.5% Mg—$Na_2$EDTA | 1-5 |
| 3% Ca—$Na_2$EDTA | 1-5 |
| 4.5% Fe—$Na_2$EDTA | 0.1-3 |
| 5% Mn—$Na_2$EDTA | 0.1-1 |
| Nonionic surfactant | 9⅔ |
| | Pounds |
| Urea | 100-300 |
| Xylose | 75-200 |
| Total | |

Example 12

Up to 2.5 gallons of Mac was formulated within the following specifications under the product name MegAleX™ and applied as a foliar spray in 100 gallons of water to 1 acre of turf. As a result, greenness of the turf was visibly enhanced. Foliar applications were repeated every two weeks, as needed.

2.5 Gal Concentrate

| | Pounds |
|---|---|
| Water | 1-20 |
| 2-propanol | 0.1 to 10 |
| 3% Mg—Na$_2$EDTA | 0.1-1 |
| 5% Mn—Na$_2$EDTA | 0.1-0.30 |
| 4.5% Fe—Na$_2$EDTA | 0.1-0.5 |
| Urea | 0.5-3 |
| Methylglucopyranosides | 5-10 |
| Non-ionic surfactant | 0.8-2 |

Example 13

TABLE 1

Estimated range of PectiC$^+$ characteristics as compared to those of native pectin. (Characteristics of native pectin from Fishman, et al 2001).

| Characteristic | Native Pectin | PectiC$^+$ |
|---|---|---|
| Least size (nm) | 13 | ~25 |
| Maximum size (nm) | 45 | ~50 |
| Low kiloDaltons | 41 | ~200 |
| High kiloDaltons | ~300 | ~350 |
| High Sugar:Pectin | >100:1 | >150:1 |
| Cations | Ca$^{2+}$ | Variable |

The following are exemplary ranges of effective application doses for rooting media based on 10 ml per plant, applied to roots and shoots.

| Plant type | Cob-component | Saccharide | Ca$^{2+}$-chelator |
|---|---|---|---|
| Geranium | 0.1% to 5% | Arabinose | (NH$_4$)$_2$EDTA |
| Rose | 0.5% to 20% | Methyl glucoside | Ammonium oxalate |
| Cabbage | 0.3% to 10% | Indican | Mg—(NH$_4$)$_2$EDTA |
| Turf | 0.01% to 80% | Xylose | (NH$_4$)$_2$EDTA Mg—Na$_2$EDTA |

Although specific features of the invention are described with respect to one example and not others, this is for convenience only as some feature of one described example may be combined with one or more of the other examples in accordance with the methods and formulations of the invention. While the preferred embodiment of the invention has been illustrated and described, it will be appreciated that various changes can be made therein without departing from the spirit and scope of the invention. Other permutations of the methods of the invention will occur to those skilled in the art and are within the following claims:

What is claimed is:

1. A living plant having at least one molecule of pectin modified with a saccharide by subjecting said pectin to a Ca$^{2+}$-chelation with a water-soluble salt of a Ca$^{2+}$-chelator-saccharide-chelant selected from the group consisting of Ca$^{2+}$-manganese-(NH$_4$)$_2$EDTA-alkylglycopyranoses, Ca$^{2+}$-manganese-(NH$_4$)$_2$EDTA-acylglycopyranoses, and thereby binding a saccharide to said pectin.

2. The living plant of claim 1, wherein said Ca$^{2+}$-manganese-(NH$_4$)$_2$EDTA-alkylglycopyranoses are selected from the group consisting of Ca$^{2+}$-manganese-(NH$_4$)$_2$EDTA-methylglycopyranoses and Ca$^{2+}$-manganese-(NH$_4$)$_2$EDTA-polyalkylglycopyranoses.

3. The living plant of claim 1, wherein said Ca$^{2+}$-manganese-(NH$_4$)$_2$EDTA-acylglycopyranoses are selected from the tetraacetylglycopyranoses and Ca$^{2+}$-manganese-(NH$_4$)$_2$EDTA-polyacylglycopyranoses.

* * * * *